(12) United States Patent
Bashir

(10) Patent No.: US 10,667,944 B2
(45) Date of Patent: Jun. 2, 2020

(54) OPHTHALMIC INTRA OCULAR ACCESS TOOL

(71) Applicant: Samer Jaber Bashir, Manama (BH)

(72) Inventor: Samer Jaber Bashir, Manama (BH)

(*) Notice: Subject to any disclaimer, the term of this patent is extended or adjusted under 35 U.S.C. 154(b) by 0 days.

(21) Appl. No.: 16/042,101

(22) Filed: Jul. 23, 2018

(65) Prior Publication Data

US 2019/0076295 A1    Mar. 14, 2019

Related U.S. Application Data

(60) Provisional application No. 62/556,781, filed on Sep. 11, 2017.

(51) Int. Cl.
    *A61F 9/00*      (2006.01)
    *A61M 5/42*      (2006.01)
    *A61F 9/007*     (2006.01)

(52) U.S. Cl.
CPC .......... *A61F 9/0026* (2013.01); *A61F 9/0017* (2013.01); *A61M 5/427* (2013.01); *A61F 9/00736* (2013.01); *A61M 2210/0612* (2013.01)

(58) Field of Classification Search
CPC .... A61F 9/0026; A61F 9/00736; A61F 9/008; A61F 9/00781; A61F 9/013; A61F 2/1662; A61F 9/0017; A61M 5/427
See application file for complete search history.

(56) References Cited

U.S. PATENT DOCUMENTS

| | | | | |
|---|---|---|---|---|
| 3,074,407 A | * | 1/1963 | Moon | A61F 9/013 606/166 |
| 4,205,682 A | * | 6/1980 | Crock | A61F 9/013 30/276 |
| 4,739,761 A | * | 4/1988 | Grandon | A61F 9/0136 606/166 |
| 5,772,675 A | * | 6/1998 | Hellenkamp | A61F 9/009 606/166 |

(Continued)

*Primary Examiner* — Matthew F Desanto

(57) ABSTRACT

This invention is a handheld multipurpose device for standardizing intraocular access for injecting into or obtaining substance(s), content(s), medicine(s), or sample(s) from a human eye(s) or an animal eye(s), in any age group(s), once a specific marker(s) is placed at corneal scleral Limbus. The device is comprising an elongated handle connected to a body having a walled structure with no spaces, one or more space(s) at the bottom; a predesigned curvature(s) in the said device to aid in placement on the surface of the eye; a set or more of track(s) with entry and exit port(s) travelling within the wall(s) at a certain angle and length; a groove that outlines the outer walls limited above and below by projections; a needle hub adapter(s) and/or receiver(s) that allows universal attachment of any injecting device(s) with an opening to the bottom of the device; a projecting marker(s) on one or more sides that indicates where the whole device should rest on the eye at the Cornea-Sclera junction called Limbus; a large opening/window at the bottom of the said device allowing access to all structures of the anterior segment of the eye; and a larger opening(s) and/or window(s) allowing a reservoir function, as well as access to posterior segment and a set of repeated projections from the underside of the device to facilitate gripping to the eye tissue underneath.

1 Claim, 11 Drawing Sheets

(56) References Cited

U.S. PATENT DOCUMENTS

| | | | | |
|---|---|---|---|---|
| 6,679,898 | B1* | 1/2004 | Chuck | A61F 9/0133 |
| | | | | 606/166 |
| 7,824,372 | B1* | 11/2010 | Kurup | A61F 9/0017 |
| | | | | 604/116 |
| 8,623,001 | B2* | 1/2014 | Preuss | A61F 9/00827 |
| | | | | 606/107 |
| 8,678,593 | B2* | 3/2014 | Abt | A61B 3/125 |
| | | | | 351/212 |
| 8,863,749 | B2* | 10/2014 | Gooding | A61F 9/00827 |
| | | | | 128/898 |
| 9,044,302 | B2* | 6/2015 | Gooding | A61B 3/14 |
| 9,144,516 | B2* | 9/2015 | Goncalves | A61F 9/0017 |
| 9,445,942 | B2* | 9/2016 | Futamura | A61F 9/00736 |
| 10,130,351 | B2* | 11/2018 | Shugarman | A61B 17/02 |
| 10,219,939 | B1* | 3/2019 | Bashir | A61F 9/00781 |
| 2003/0060763 | A1* | 3/2003 | Penfold | A61F 9/0017 |
| | | | | 604/116 |
| 2004/0147944 | A1* | 7/2004 | Lahaye | A61F 9/009 |
| | | | | 606/166 |
| 2005/0288697 | A1* | 12/2005 | Tei | A61B 17/3403 |
| | | | | 606/166 |
| 2010/0318034 | A1* | 12/2010 | Goncalves | A61F 9/0017 |
| | | | | 604/174 |
| 2011/0022035 | A1* | 1/2011 | Porter | A61F 9/00825 |
| | | | | 606/4 |
| 2014/0276673 | A1* | 9/2014 | Heitel | A61F 9/009 |
| | | | | 606/4 |
| 2016/0270956 | A1* | 9/2016 | Lin | A61F 9/0017 |
| 2017/0258637 | A1* | 9/2017 | Seiler | A61B 90/39 |
| 2017/0266045 | A1* | 9/2017 | Kangastupa | A61F 9/0026 |

* cited by examiner

OPHTHALMIC INTRA OCULAR ACCESS TOOL

CROSS-REFERENCE TO RELATED APPLICATIONS

The present application claims priority to U.S. provisional patent application Ser. No. 62/556,781, filed on Sep. 11, 2017. The entire disclosure is included herein in its entirety at least by reference.

BACKGROUND OF THE INVENTION

1. Copyright Notice

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Field of the Invention

The present disclosure relates to medical and surgical ophthalmological tools.

3. Discussion of the State of the Art

Millions of eyeball injections occur daily around the world either to inject a substance e.g. medicine or withdraw contents from inside. Such access is obtained without any standardization and varies greatly depending upon experience and training of personnel.

The usual way of gaining access to the inside of the eye has high potential of damage to the eye or complicating a simple task.

The current practice is to open the eye with a device called speculum to spread the eyelids exposing most of the front of the eye including visual axis. Surface of the eye is then washed, disinfected and numbed using many medicines. Then a measuring device similar to a miniature ruler called caliper is applied from the corneal Limbus (junction of cornea and sclera) to a set distance of the operator choosing. Then the injection is given at a variable angle and penetration. The same procedure is done to obtain contents of the eyeball. Age of the patient, status of the eye and movement of the patient eyes are variables, which could and does lead to complications affecting the health of the eye intended to be treated. The skill and experience of the operator are also variables causing high risk. There is not a single device to serve as a safe standard for gaining access, which is skill, training, age, species and anatomical variation dependent.

The only prior art, application and scope with only one specified port at 3.5 mm from the Limbus. U.S. Pat. No. 9,144,516 B2 claims facilitating administration only (not obtaining) through a single port for injection set only at 3.5 mm. The device provides no claim for intraocular access including but not limited to withdrawal in the form of taking sample(s) for testing or to alter the content(s) of the eye or to alter the pressure of the eye ball. It also does not claim varying distances or angles to the said procedure. The said device also does not support adjustability to various eye conditions in different ages. This can range from premature babies to children to full-grown adults with different intraocular Lens conditions ranging from Aphakia (no Lens either natural or artificial inside the eye), Phakia (Natural Lens is still in its place inside the patient's eye) or even in cases of pseudophakia (Artificial implanted Lens inside the eye). This said prior art also uses an annular support system, which is totally different from our device in use.

All of these disadvantages work together to affect general wellbeing of eyes through many variables resulting in many complications seen daily at various health care facilities. Therefore, the need exists in the field of diagnostic and therapeutic eye care in humans as well as animals, for a standardized access-granting tool to the contents of the eye in any age group. Such tool is desperately missing and our invention provides the answer. The present invention provides such a method and the overall combination of these features is nowhere disclosed in the prior art cited above which appears to be representative of the general art in this area although it is not intended to be an all-inclusive listing of pertinent prior art patents.

SUMMARY OF THE INVENTION

In light of the disadvantages of the prior art, the following summary is provided to facilitate an understanding of some of the innovative features unique to the present invention and is not intended to be a full description. A full appreciation of the various aspects of the invention can be gained by taking the entire specification, claims, drawings, and abstract as a whole.

The present invention seeks to provide a solution to this problem(s) by providing a handheld multipurpose device for standardizing intraocular access for injecting into or obtaining substance(s), content(s), medicine(s), or sample(s) from a human eye(s) or an animal eye(s), in any age group(s), once a specific marker(s) is placed at corneal scleral Limbus.

Preferably, in one embodiment of the present invention, a set guidance track(s) with entry and exit port(s) is pre designed to provide specific distance and angles, facilitating and granting access for injecting into or obtaining substance(s), content(s), medicine(s), or sample(s) from a human eye(s) or an animal eye(s), in any age group(s).

Preferably, in another embodiment of the present invention, a set space is pre designed to provide access for injecting into or obtaining substance(s), content(s), medicine(s), or sample(s) from a human eye(s) or an animal eye(s), in any age group(s).

Preferably, in yet another embodiment of the present invention, a set groove and protruding edges are pre designed to provide eyelids separation facilitating access for injecting into or obtaining substance(s), content(s), medicine(s), or sample(s) from a human eye(s) or an animal eye(s), in any age group(s).

Preferably, in another embodiment of the present invention, an adapter(s) and/or receiver(s) is pre designed to provide one-handed access for injecting into or obtaining substance(s), content(s), medicine(s), or sample(s) from a human eye(s) or an animal eye(s), in any age group(s).

This Summary is provided merely for purposes of summarizing some example embodiments, so as to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE DRAWING FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
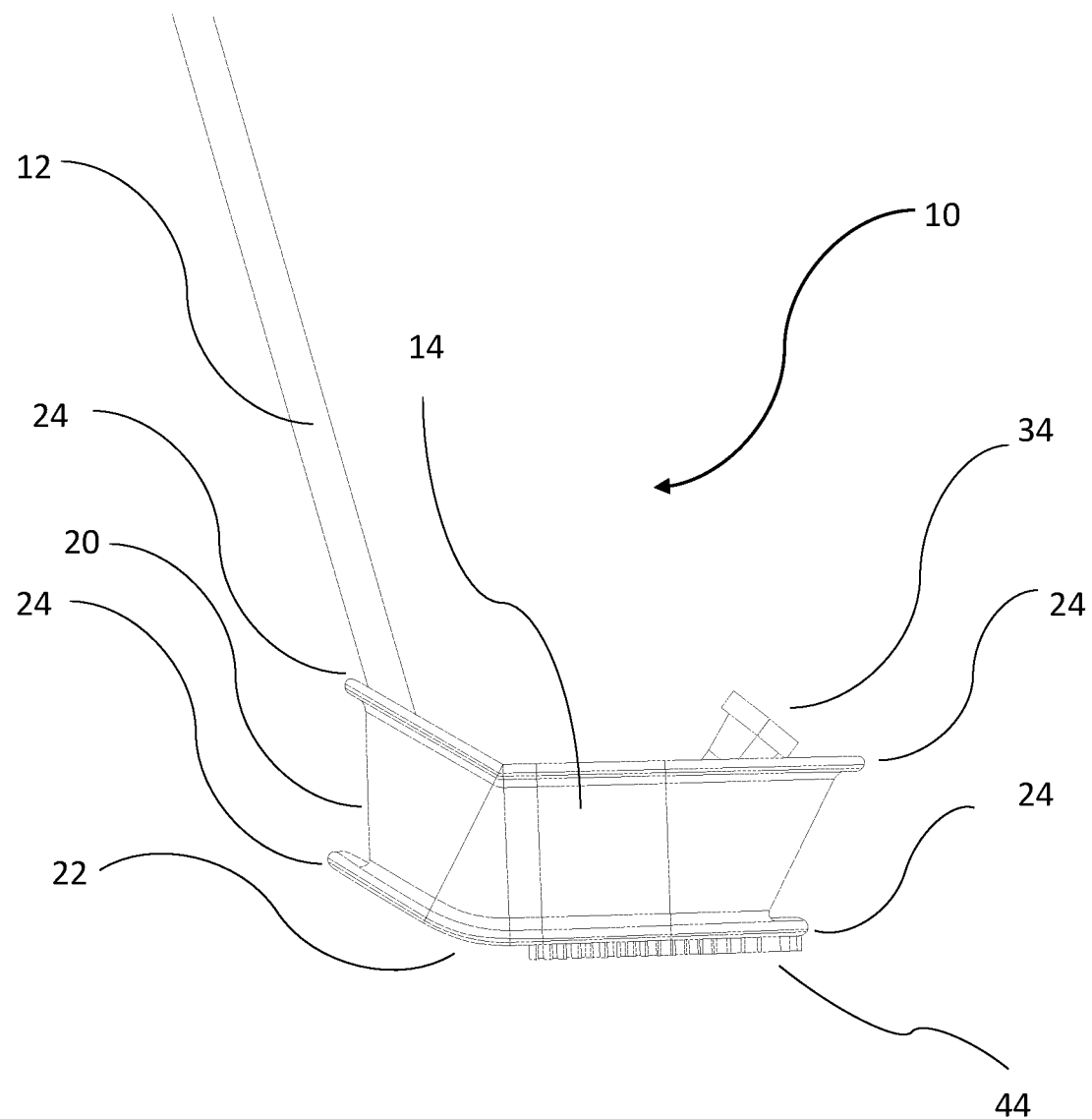
FIG. 1 shows an elevation view from the side of the device according to an embodiment of the present invention.
Figure 2:
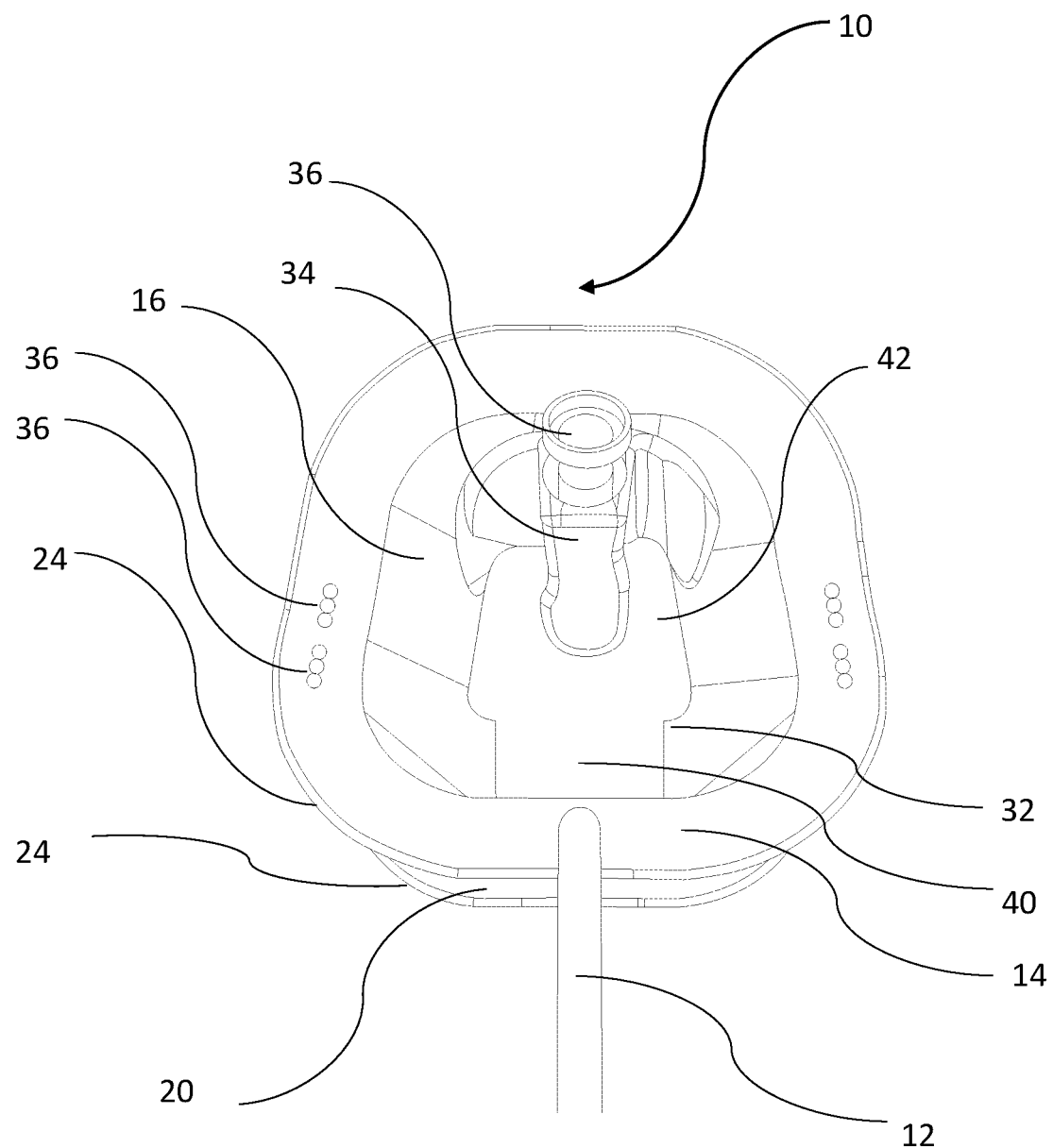
FIG. 2 illustrates a top view of FIG. 1 according to an embodiment of the present invention.
Figure 3:
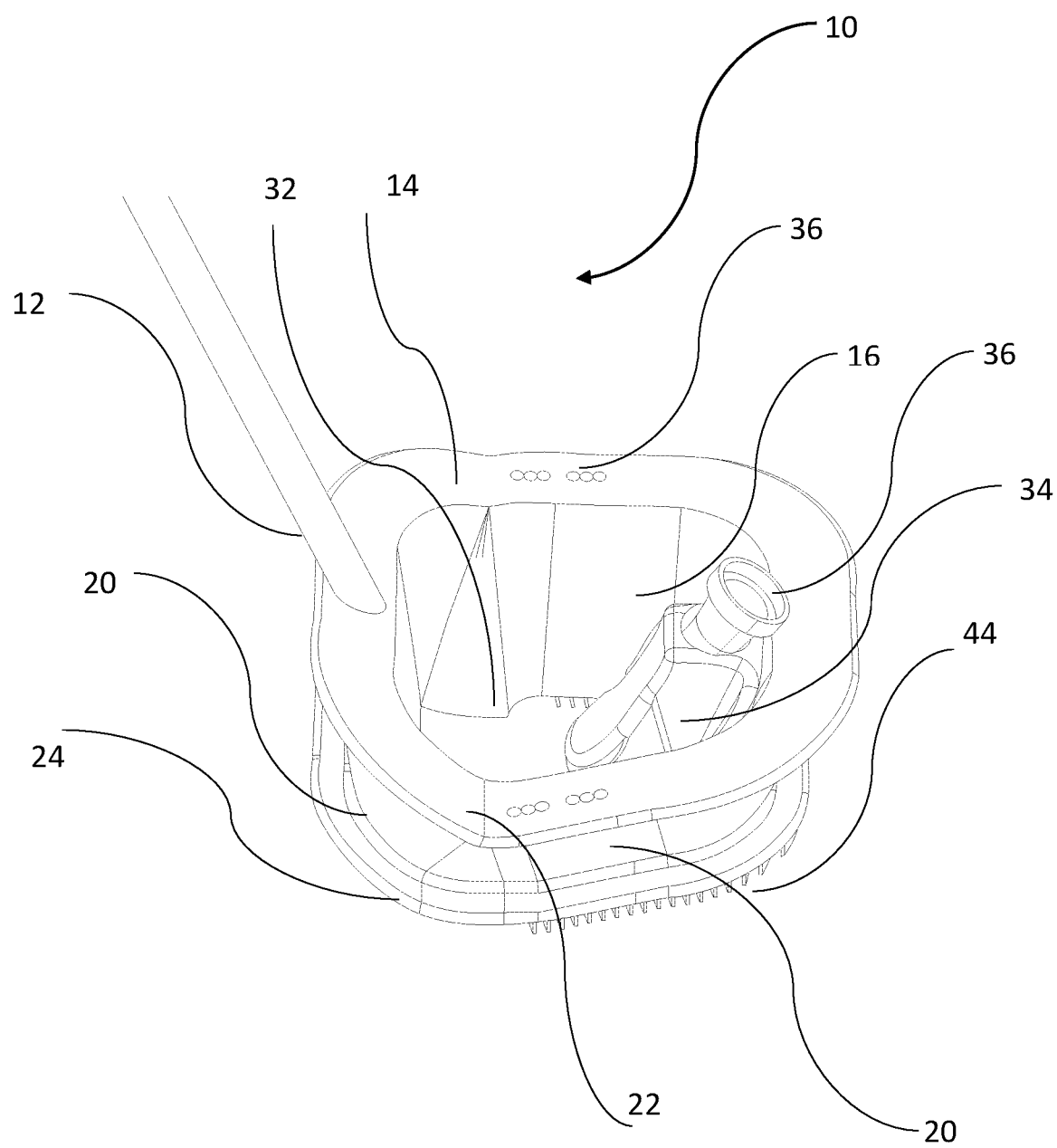
FIG. 3 shows an elevation view from the oblique side of the device according to an embodiment of the present invention.
Figure 4:
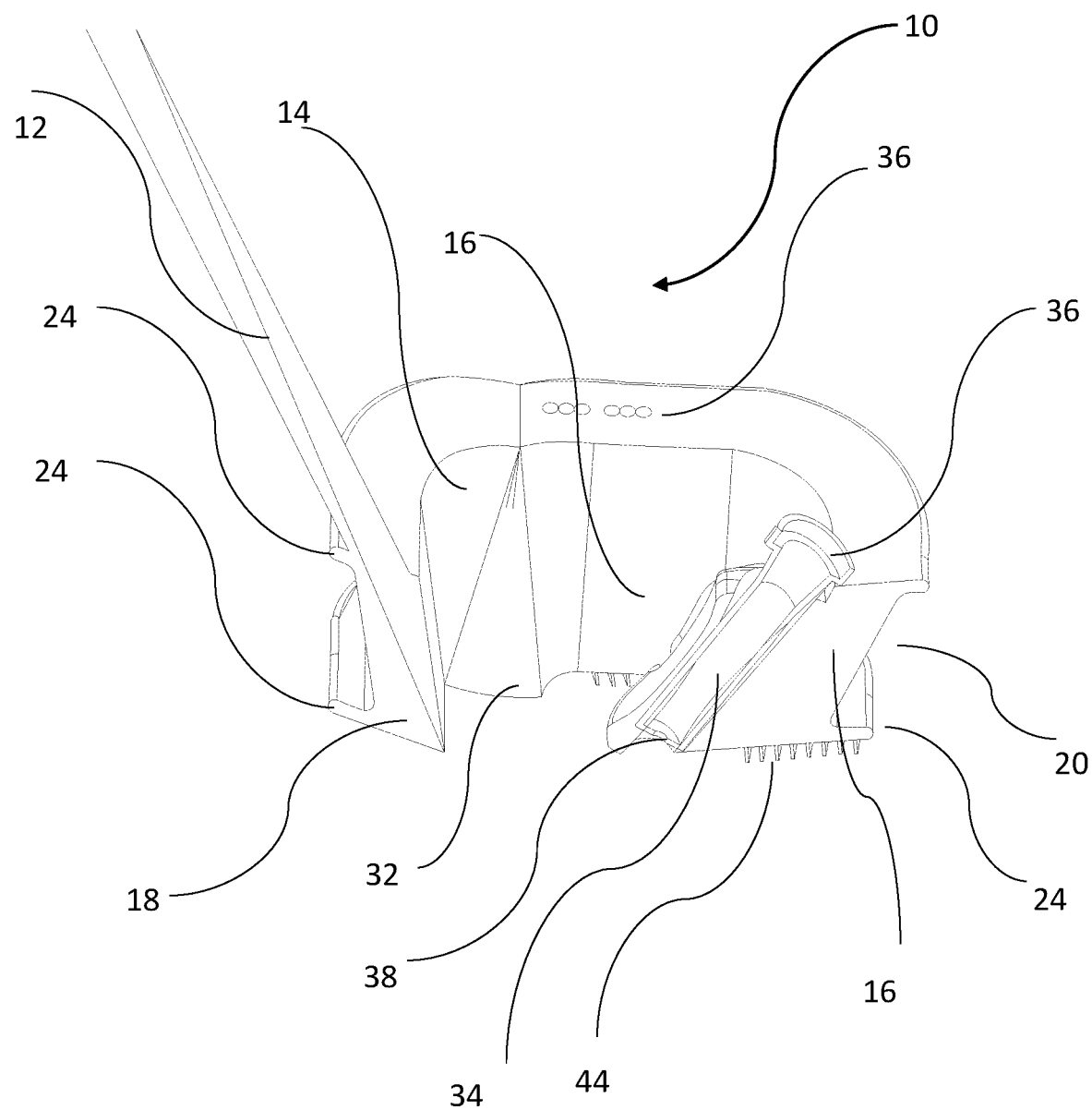
FIG. 4 shows a section view from front to back of the device of FIG. 1 according to an embodiment of the present invention.
Figure 5:
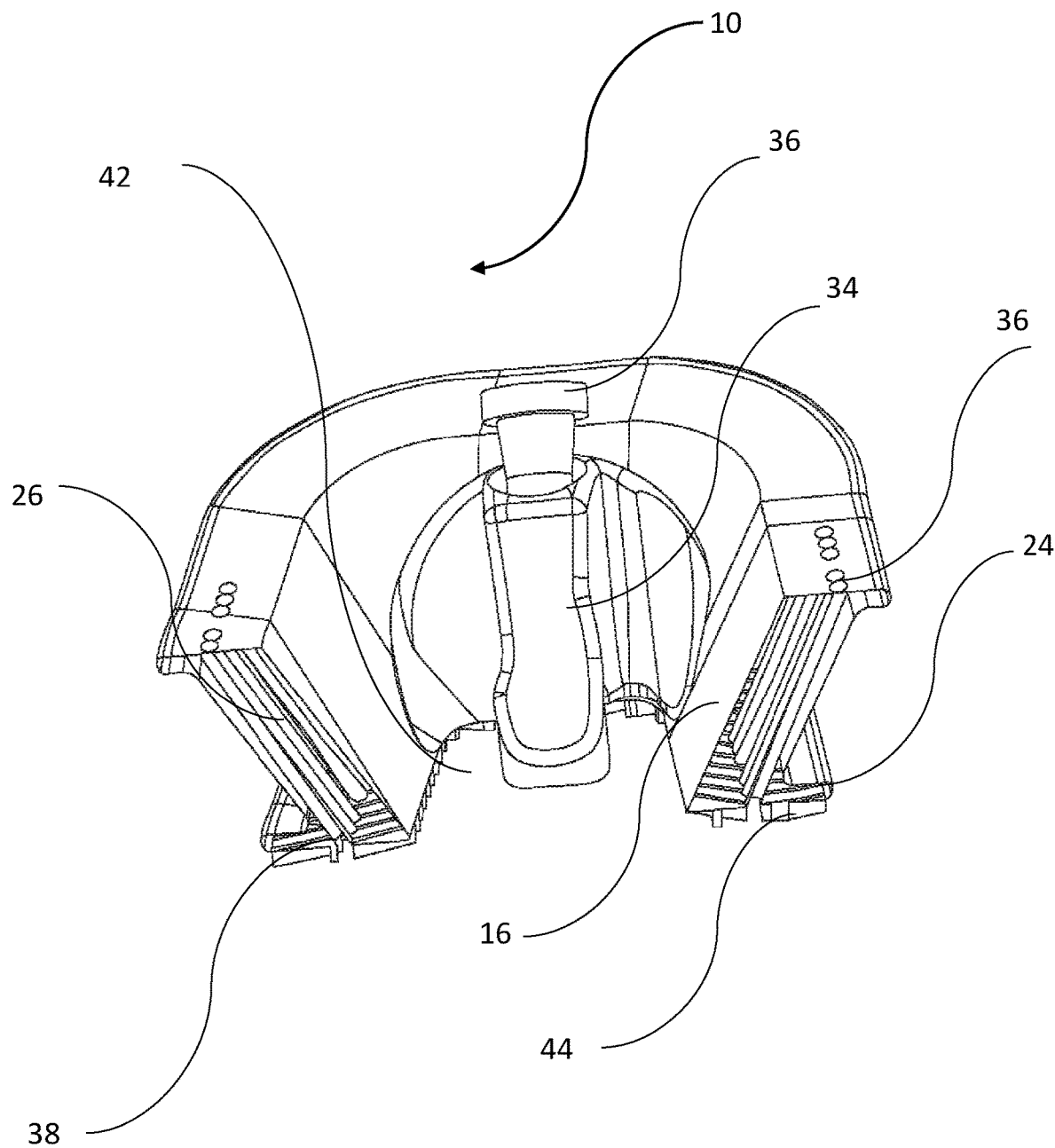
FIG. 5 shows a section view from one side to another showing distal end of the device of FIG. 1 according to an embodiment of the present invention.
Figure 6:
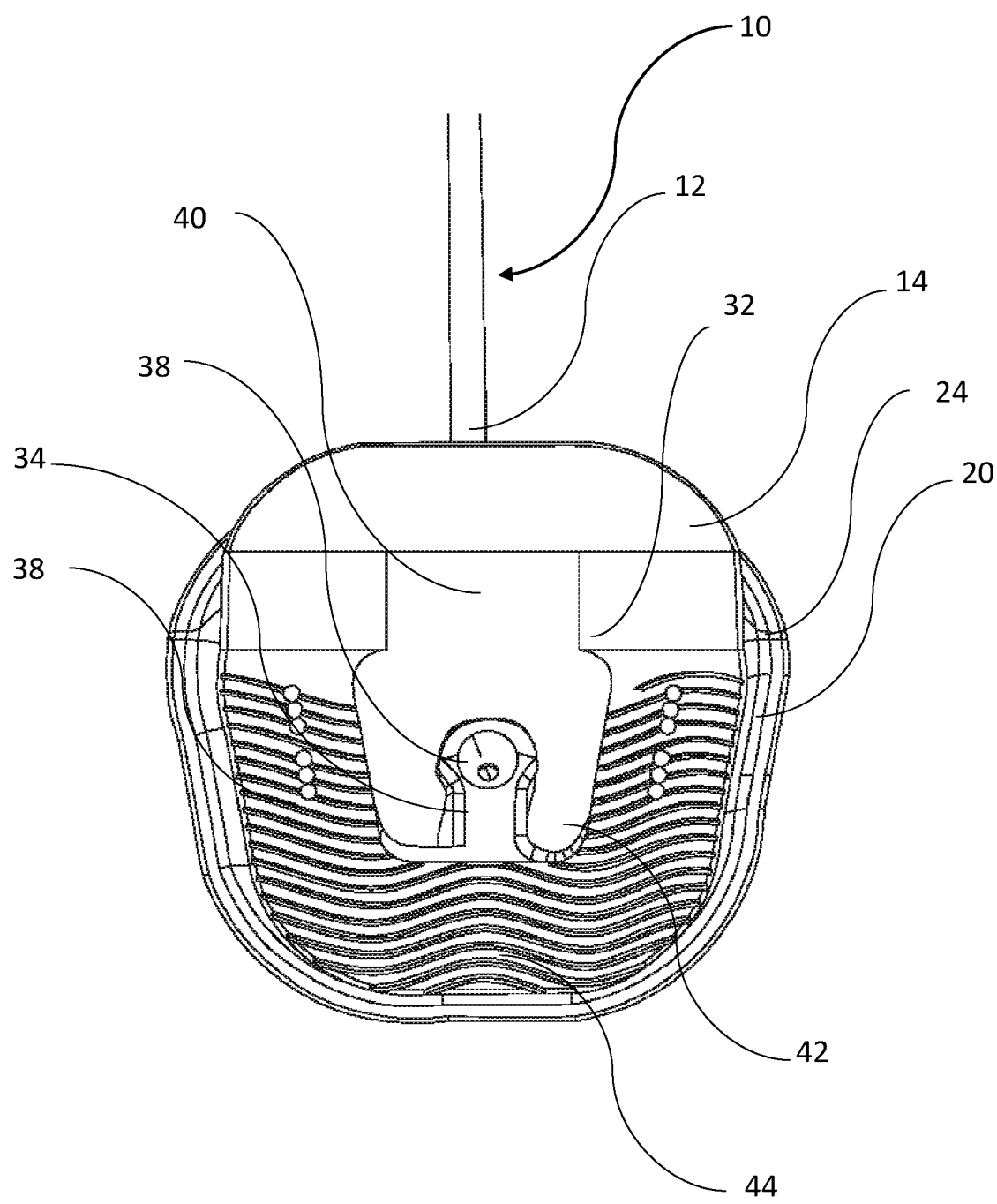
FIG. 6 shows an elevation view from the bottom of the device according to an embodiment of the present invention.
Figure 7:
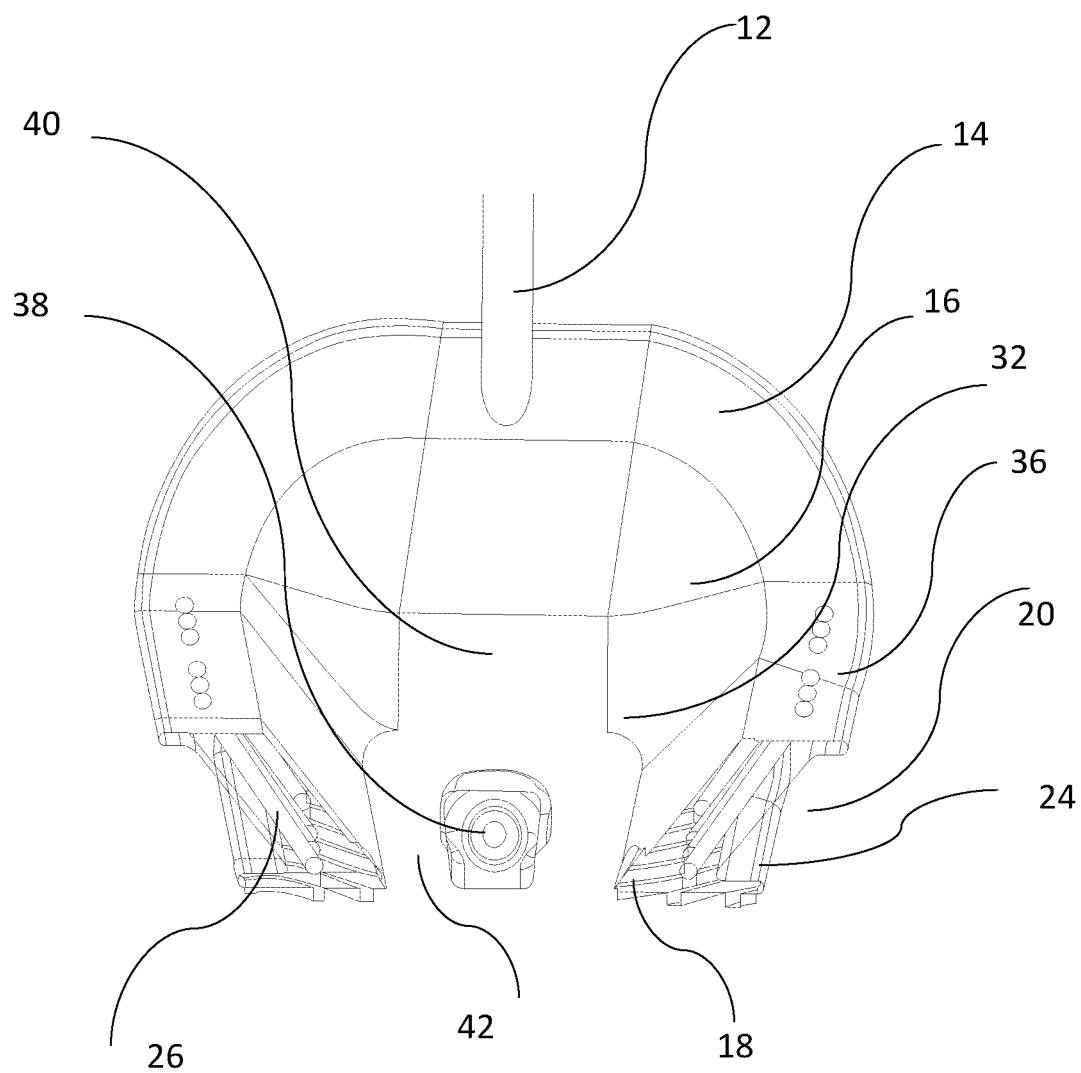
FIG. 7 shows a section view from one side to another showing proximal end of the device of FIG. 1 according to an embodiment of the present invention.
Figure 8:
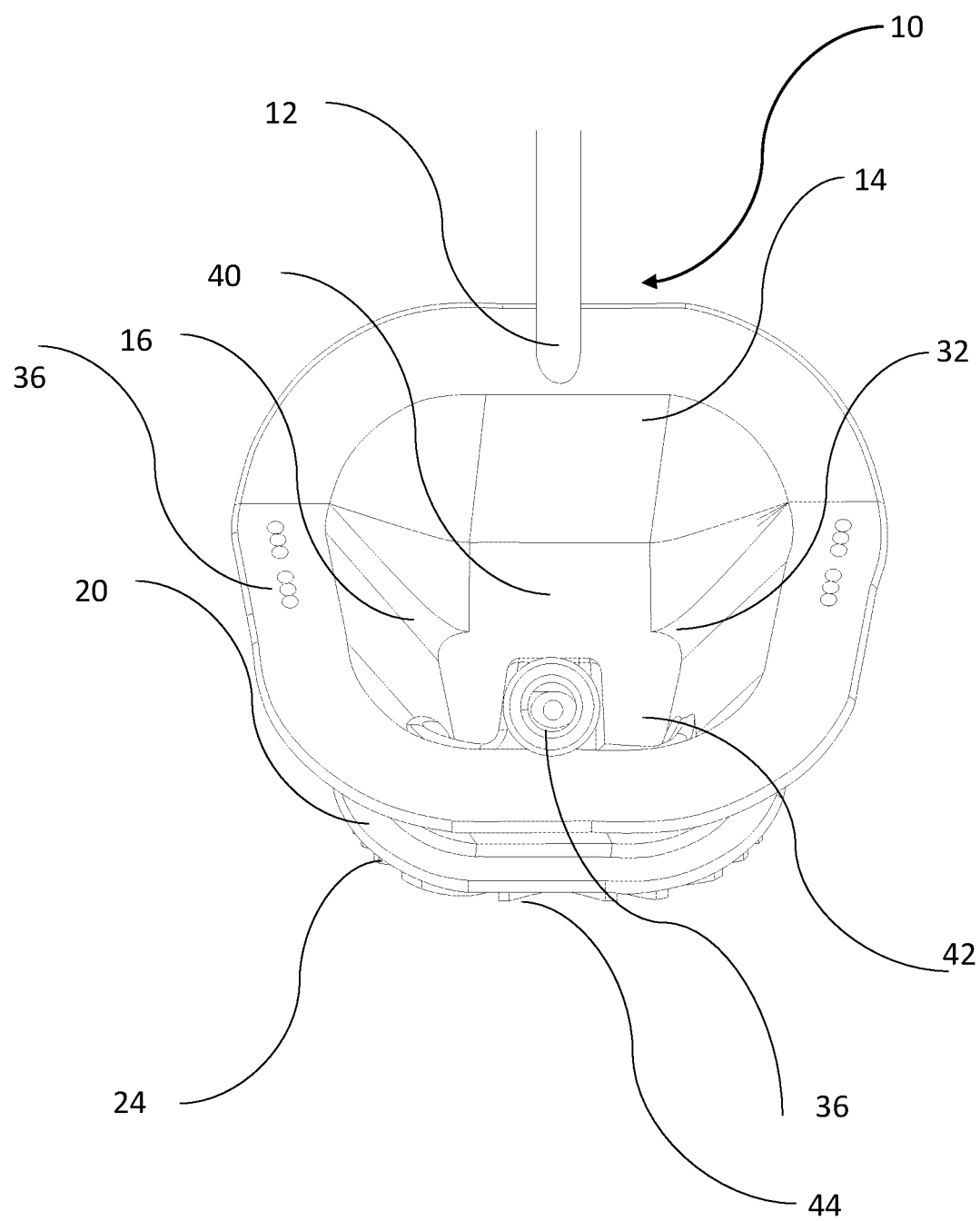
FIG. 8 shows an elevation view from the oblique side of the distal end according to an embodiment of the present invention.
Figure 9:
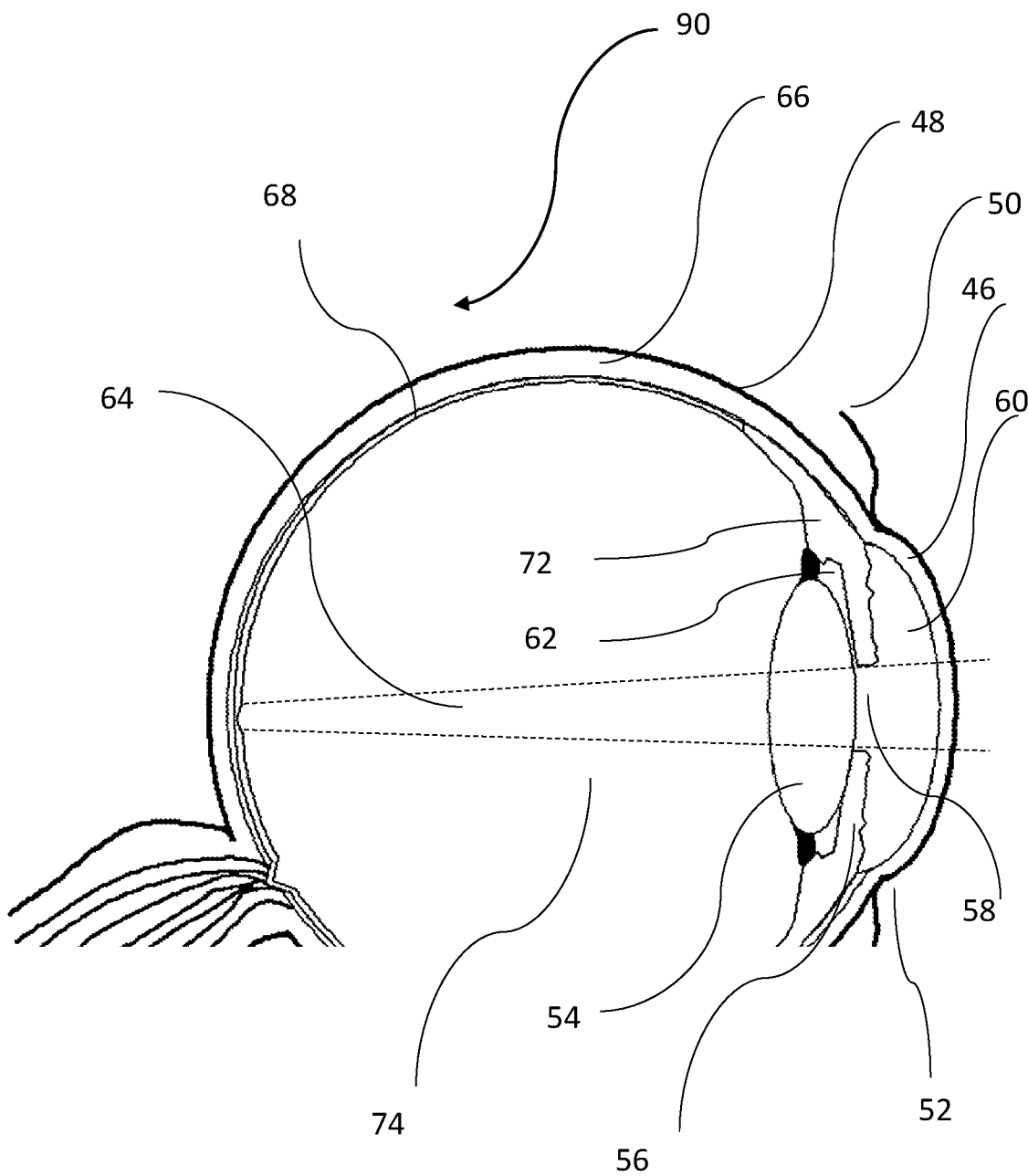
FIG. 9 shows a section view of an eye to highlight anatomical structures.
Figure 10:
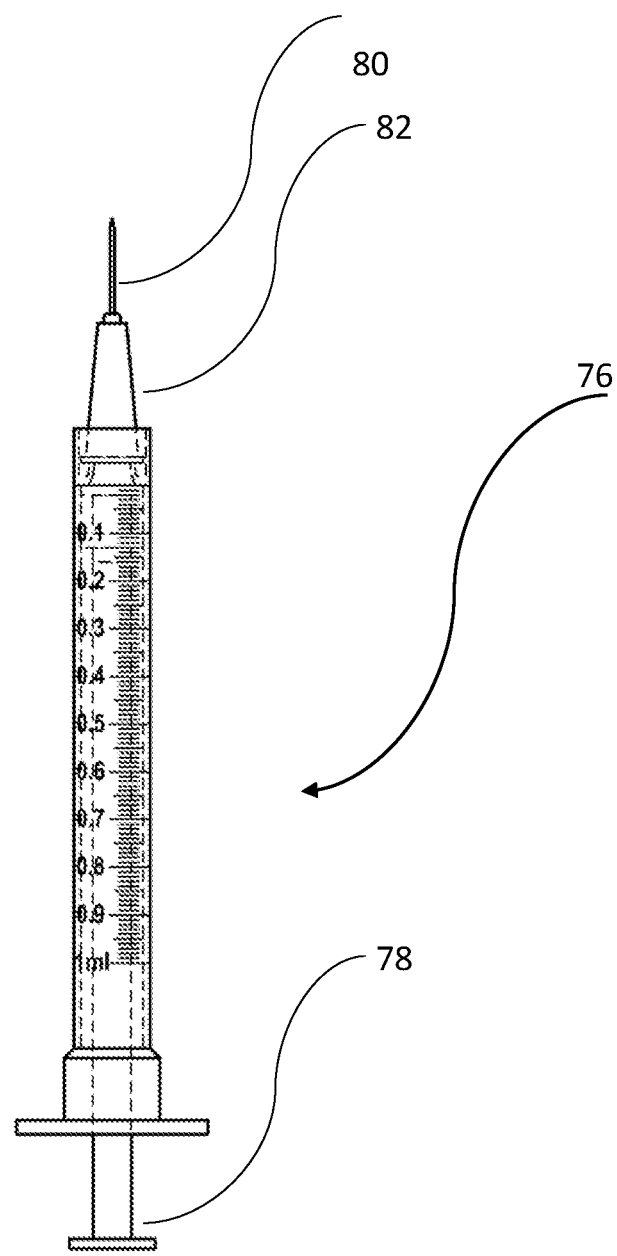
FIG. 10 shows a schematic of a syringe with its parts explained.
Figure 11:
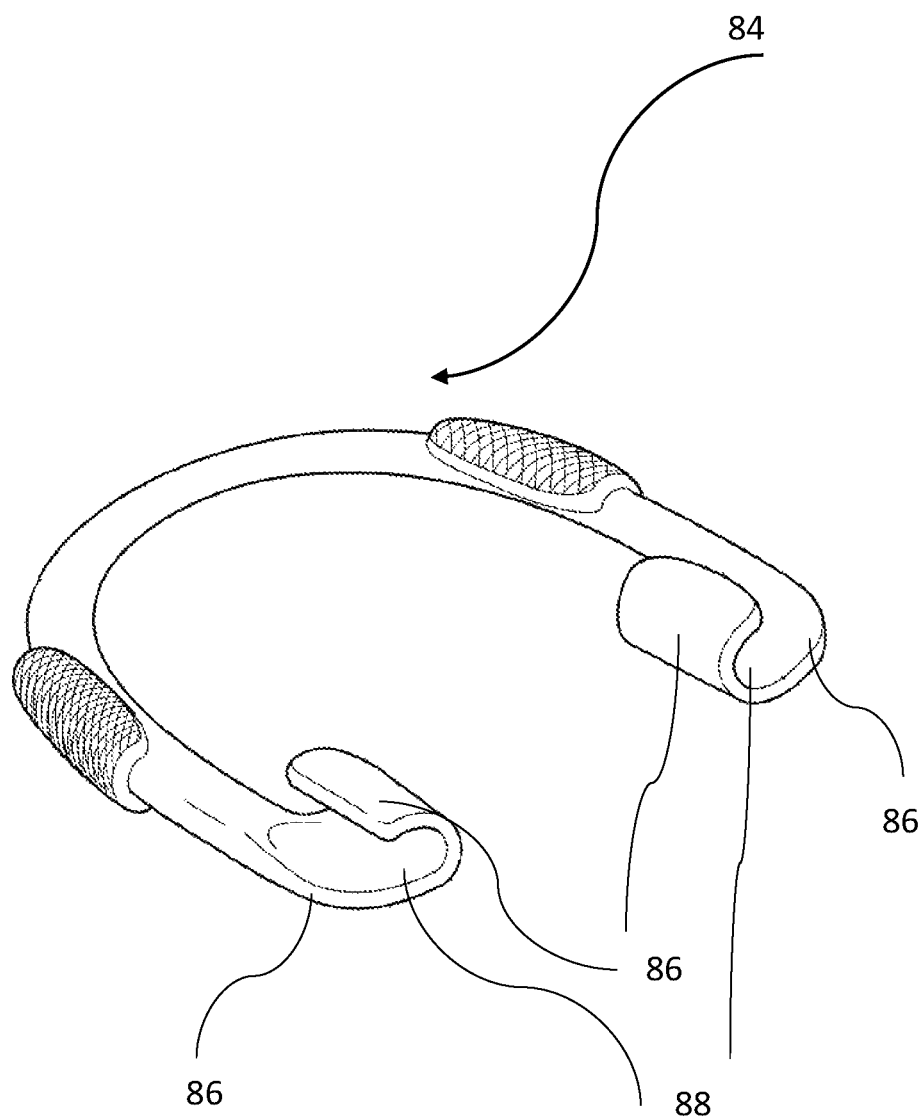
FIG. 11 shows a schematic of a speculum with its parts explained.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Before explaining the invention in detail, it is to be understood that the invention is not limited in its application to the detail of application illustrated in the drawings since the invention is capable of other embodiments and of being practiced or carried out in various ways. It is also to be understood that the phraseology or terminology employed is for the purpose of description only and not of limitation. The present invention is described in enabling detail in the following examples, which may represent more than one embodiment of the present invention.

In use, a handheld multipurpose device, an Ophthalmic Intra Ocular Access Tool 10 for standardizing intraocular access for injecting into or obtaining substance(s), content(s), medicine(s), or sample(s) from a human eye(s) 90 or an animal eye(s) 90, in any age group(s), once a specific marker(s) 32 is placed at corneal scleral Limbus 52. The Ophthalmic Intra Ocular Access Tool 10 also simplifies the procedure by eliminating at least two more tools; an eyelid opening and separating tool called "Speculum" 84 and a measuring device called "Caliper" that were complicating the usual procedure.

The Ophthalmic Intra Ocular Access Tool 10 can be for a single use (disposable) or for multiple uses (reusable) after industry's standard protocols of disinfection are properly applied. The Ophthalmic Intra Ocular Access Tool 10 can be sold in an unsterile status with warning of necessary disinfection before use, sterile in a suitably designed pack ready for use by the operator or even as a customizable 3D file ready for 3D printers.

This Ophthalmic Intra Ocular Access Tool 10 has a handle 12 to be held by the operator. The handle 12 can have different shapes, forms, lengths, thickness or designs to suit the purpose. One purpose is fashioning the handle 12 in such a design to allow right or left-handed operation. In another embodiment, this said handle 12 could also be integrated fully with the rest of the Ophthalmic Intra Ocular Access Tool 10 or separate to be attached manually to suit the operator needs. The final embodiment of the handle 12 can change to adapt to manufacturing techniques and to make sure the device is well handled and fixed.

At the end of this handle 12 is an oval shaped body 14 with a space(s) in the center that represents the bulk of the Ophthalmic Intra Ocular Access Tool 10. In another embodiment, the body 14 is round in shape, diamond or triangular. In another embodiment, the body 14 can assume any shape to suit the purpose taking into consideration the huge variables of sizes of eyes 90 this tool may be designed for. The animal species variable alone is responsible for many embodiments, which are dictated by the application at hand.

The whole body 14 of the Ophthalmic Intra Ocular Access Tool 10 is curved either permanently or can be changed manually to suit the purpose. The curvature(s) 22 helps greatly in mimicking the shape of the outer eye 90 wall in human eyes 90 as well as animal eyes 90 to facilitate fixation as well as granting access. The said curvature(s) 22 can also be varied to uniquely adapt to different age group(s) including premature baby(s) needing injection into or obtaining various fluid(s) or tissue(s) in a form including but not limited to sample(s) or biopsy(s). In other embodiments, the curvature(s) 22 is set in such a way to specifically suit a single animal or a group of similar eyes 90 of different animals either from one or more than one species. In yet another embodiment the Ophthalmic Intra Ocular Access Tool 10 may be perfectly flat to suit the purpose(s) and the operator(s).

The body of the device 14 also contains walls 16 that are designed in sloping Angle(s) 18 of fixed or variable degrees. These said wall(s) 16 run in all 360 degrees fashion to form a structure capable of supporting different functions. On the outer aspect of these said wall(s) is a groove(s) 20 of variable dimensions and depth to separate then hold the eyelids open either in humans of any age group(s) or in animal(s) requiring access to intraocular content(s) 90. In this example, the groove(s) 20 resembles the groove(s) on a speculum 88. The groove(s) 20 is limited at its upper and lower edges by projection(s) or rim(s) 24 simulating speculum blade(s) 86 that also run with the groove(s) 20 in 360 degrees fashion. In other embodiments, the size and shape of these wall(s) 16 including the groove(s) 20 and the limiting projection(s) 24 can change to suit the purpose and or size of the eye(s) 90 either in humans or in animal(s).

The Ophthalmic Intra Ocular Access Tool 10 size is configured in such a way along with wall(s) 16, groove(s) 20 and lid-limiting projections 24 to keep the visual axis of the patient 74 (human or animal of any age group) covered. The eye 90 is not supposed to see the procedure, the injecting or withdrawing needle(s) or trocar(s) 80. The eye 90 even does not see any drops, fluid(s) or gel(s) being introduced to the eye itself 90 before, during or after the procedure is accomplished. Such intended design with obstruction of visual axis 74 greatly increases patient(s) comfort and eases the whole procedure. The same design feature decreases cornea 46 and/or conjunctiva 50 dryness that is a side effect of such procedures. Thus wetting of ocular surface is unaffected by non-moving lids. Another useful function is avoiding ocular or orbital muscular spasm resulting from straining against the speculum 84 either in the operated upon eye 90 or the other non-affected eye 90.

These wall(s) 16 also support a series of predesigned track(s) and/or tunnel(s) 26 that run through them. The track(s) and/or tunnel(s) 26 are preplaced in specific distances, lengths and Angle(s) to suit the purpose. In other embodiment of this Ophthalmic Intra Ocular Access Tool 10, the track(s) and/or tunnel(s) 26 run in different angle(s) 18 in right or left side or exactly the same in one or more wall(s) 16. In other embodiments, the track(s) and/or tunnel(s) 26 is also preplaced on one, two, three or all four wall(s) 16 depending upon a specific purpose. This design is intended to produce many options suiting specific purposes for use in humans or animals, which vary greatly. The entry port(s) 36 are on top of the wall(s) 16 facing the operator while the exit port(s) 38 rest on the eye wall 90. This mode of operation standardizes access each time a needle 80, trocar or any sharp device goes through taking medicine(s), therapeutic or diagnostic agent(s) or obtaining some form of fluid(s), tissue sample(s) or any other content for diagnostic as well as therapeutic purposes in humans or animals in any age group. The track(s) and/or tunnel(s) 26 can be as little as single in one embodiment or multiple at different distances or Angle(s) 18 or lengths to suit the purpose of injecting into or obtaining from the eye 90 in humans or animals in any age groups. Fixing the access track(s) and/or tunnel(s) 26 to a specific angle(s) 18, distance and caliber guarantees exact access every time regardless of operator skills, operator experience, patient (human or animal), eye 90 or body movement, and patient (human or animal) sense of pain or fear and above all regardless of the condition(s) requiring such access. In many cases, this track(s) and/or tunnel(s) 26 can provide means to release pressure from the eye 90 to a desired level either relieving a disease or preventing high intraocular pressure (therapeutic or prophylactic). A predefined and anticipated track(s) and/or tunnel(s) 26 can in other embodiments change along with the disease process or new advances in medicine. Such track(s) and/or tunnel(s) 26 can be modified in form and function to keep up with newer injecting needles 80 of different calibers or sampling devices of different needs for different purposes.

In other embodiment(s), the wall(s) 16 are sloped in a specific angle(s) 18 from the inside to allow free form access and penetration of eyeballs guided by their inner slopes. These said slopes provide guidance angle(s) 18 in case the operator wants to control depth of penetration manually but keeping a set angle(s) of penetration. Such configuration also allow space for expansion in case of larger caliber needle(s) 80 or trocar(s) not suitable to go through predefined track(s) and/or tunnel(s) 26. In other embodiment, different wall(s) 16 can have different slopes at different Angle(s) 18 extending the range of such procedures.

This multipurpose Ophthalmic Intra Ocular Access Tool 10 also supports a predesigned needle hub 82 adapter(s) and/or receiver(s) 34 to allow complex single-handed access to the eye 90. In one embodiment, the adapter(s) and/or receiver(s) 34 is designed to receive a preset needle 80 or trocar to suit the purpose while in other embodiment the hub receiver(s) 34 is universal suiting any form of sharp object intended for the purpose. Yet in other embodiments, the needle hub 82 adapter(s) and/or receiver(s) 34 can be just one or multiple depending upon the intended use. Such said receiver 34 is designed for supporting the injecting or withdrawal device e.g. a syringe 76 while the plunger 78 or activating mechanism is operated using single hand. Such operation can also be automated by a machine, which may be activated via a foot pedal or even by another operator as the injecting, or the withdrawing device is fixed along with the tool. Such design can allow for complex and simultaneous injection and withdrawal procedures not possible before. Some disease entities require complex substitution of contents or filling of vacuum created by withdrawal or equalization of pressure inside the eye 90 to accomplish safe procedures. The entry port(s) of this adapter(s) and/or receiver(s) 36 is usually at the top of the device facing the operator while the exit port(s) 38 at the bottom of the Ophthalmic Intra Ocular Access Tool 10 facing the eye. The exit port(s) 38 can be set at any distance or angle(s) 18 to suit the purpose including but not limited to penetration depth.

The space in the center of the body of the said device 14 has none, one, two or more window(s), which are spread either apart or in other embodiment, connected to each other but with different locations and dimensions. In other embodiments, the space can also be very small, single or elongated. In yet another embodiment the space can even be absent to suit the intended purpose. The space nearest to the operator is called the anterior segment window(s) 40 designed to give access to the anterior segment of the eye including but not limited to the following anatomical structures: Cornea 46, Sclera 48, Limbus 52, Iris 56, Lens 54, anterior chamber 60 and posterior chamber 62 of the eye 90 whether human eye or animal eye, in any age group. The access granting space 40 is designed so that the operator can also observe changes including but not limited to extent and angle(s) 18 of penetration, sudden pressure changes, corneal transparency, bleeding, inadvertent penetration of some ocular structures and other anatomical 90 changes accompanying the injecting or withdrawal procedures. This space 40 also allows easy access that serves many purposes, one of which is enabling paracentesis or withdrawal of eyeball 90 contents in front of Iris 56. It also allows free form of injecting and/or withdrawal in a standalone fashion. This space 40 may also contain a one or more predefined track(s) and/or tunnel(s) 26 similar to those in the wall(s) 16 to a preset angle(s) 18, depth and place of penetration to anterior segment of the eye to suit the purpose. Many embodiments are possible due to great anatomical variations in humans as well as animal eyes 90 of different ages and or species.

The second space 42 at the middle of the Ophthalmic Intra Ocular Access Tool 10 can be separate from anterior segment window(s) 40 or connected to it in other embodiment(s). This space called posterior segment window(s) 42, serves many functions including but not limited to the following. Providing access to normal or diseased ocular structures as Conjunctiva 50, Sclera 48, Choroid 66, Retina 68, Vitreous and Vitreous cavity 64 of the eye 90 whether human eye or animal eye. This said space 42 could be effectively used for injecting or withdrawing substance(s), content(s), medicine(s), or sample(s) or even surface or deep biopsy of aforementioned structure(s) 90. The space 42 is effectively large enough for larger caliber injection needle(s) 80 and/or trocar(s) being inserted into the eye 90 in a free form aided by the designed sloped wall(s) 16 attaining a perfect angle(s) 18 every time. In other cases if the operator wishes, a fully manual technique, access can also be granted through this space 42. The operator decides when the eye 90 needs a special technique, angle(s) 18 or penetration depth. The same applies to newer injectors with custom needle(s) 80 out of the usual design or form.

This said space 42 also serves as a reservoir for containing medicines necessary before, during and after the access routine. These medicines can be to numb the eye 90 (anesthetic(s)), to clean (normal saline or Balanced Salt Solution (BSS)), to disinfect (Povidone-iodine or similar solution(s)) or to prevent contamination later (Antibiotic(s)). Such design allows the intended substances to stay longer effectively at the access location increasing efficacy, decreasing frequency and preventing such fluids from escaping out of effective area and into the patient cheeks. Such arrangement also decreases wiping excess fluid actions by the operator allowing more control of the procedure at hand. This also increases patient comfort and decreases apprehension usually associated with such procedure(s) by decreasing tactile feedback from the peri-orbital area and lids.

Separating the two space(s) and/or window(s) 40 and 42 is one or more marker(s) 32 on the wall(s) 16 of the Ophthalmic Intra Ocular Access Tool 10 indicating where the Ophthalmic Intra Ocular Access Tool 10 should rest on the eye 90. In other embodiments, the marker(s) 32 is placed directly on the body of the device 14 if no space or reservoir is required. This said marker(s) 32 is well marked and protrudes from the sides to allow for non-mistakable placement on the Cornea 46-Sclera 48 junction called Limbus 52. This step is essential to safe operation of the Ophthalmic Intra Ocular Access Tool 10. In other embodiment, this marker(s) 32 can only be a notch or raised area or any other shape to suit the purpose. The marker(s) 32 is designed in a way to facilitate view of the Limbus 52 and not to confuse the operator in any way. The marker(s) 32 can be of the same color as the rest of the Ophthalmic Intra Ocular Access Tool 10 and in other embodiment(s), it can be of different color, shape or even material to the rest of the Ophthalmic Intra Ocular Access Tool 10. The Ophthalmic Intra Ocular Access Tool 10 can contain a visual aid(s) or magnifier(s) to help identify and correctly place the marker(s) 32 in the intended location 52 for safe operation.

The bottom part of the Ophthalmic Intra Ocular Access Tool 10 is covered with a projection(s) and/or pattern(s) 44 which can be in the shape of wavy protrusions designed in specific depth to stabilize the device even further, preventing the eyeball 90 from moving around minimizing damage and facilitating the procedure. In other embodiment(s), the pattern(s) 44 of these projections can vary in shape, size, projection height and extent to facilitate gripping to the eye 90 tissue underneath. In yet another embodiment, the underlying projection(s) and/or pattern(s) 44 can be made from the same material of the Ophthalmic Intra Ocular Access Tool 10 or different materials while in other embodiment the projection(s) and/or pattern(s) 44 can be fixed upon manufacture or assembled by the operator to suit the intended purpose. This said projection(s) and/or pattern(s) 44 also acts in a fashion to evenly spread medicine(s), antibiotic(s), anesthetic(s) or any other fluid(s) or gel(s) in the reservoirs(s) 42 described above. Such design allows these substances to reach injection port(s) exit(s) 38 maximizing their effect while containing these substances for a while. Such function also decreases the need for continuous wiping of over spelled liquids draining on the patient's cheeks causing discomfort and operator's distraction.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter. It will also be apparent to the skilled artisan that the embodiments described above are specific examples of a single broader invention, which may have greater scope than any of the singular descriptions taught. There may be many alterations made in the descriptions without departing from the spirit and scope of the present invention.

The invention claimed is:

1. A handheld multipurpose device for standardizing intraocular access for injecting into or obtaining substance(s), content(s), medicine(s), or sample(s) from an eye once a marker is placed at a Corneal-Scleral Limbus, the device comprising:

a handle having a first end and a second end configured to be used by a right or left handed operator;

a body which receives one end of said handle, said body having a bottom portion and a walled structure with at least one space having at least one window formed within said walled structure, said body having a curvature configured for mimicking the shape of an outer eye surface, said curvature is adapted to be fixed or changeable;

said wall structure further comprising multiple wall sections, wherein each wall section has a slope of a specific angle and at least two wall sections have different slopes at different angles, wherein said wall structure further includes at least one track, wherein each track has an entry and an exit port travelling within said wall structure, and said wall structure having an outer surface that includes an upper and a lower projection forming a groove that runs around said body of the device, said groove is configured to spread and retain eyelids, wherein a height, width and angle of said groove and projections are capable of being changed;

said at least one space having said at least one window includes a first window configured to allow access to an anterior segment of the eye and a second window forming a reservoir, said reservoir being configured for retaining medicine, antibiotic, anesthetic or any other fluid or gel, and allowing access to Conjunctiva, Sclera, Choroid, Retina, Vitreous and Vitreous cavity of the eye;

at least one projecting marker protruding from an inner surface of said wall structure, wherein said at least one projecting marker is configured to facilitate viewing and placement of said device on the Cornea-Sclera Limbus, wherein said at least one projecting marker may optionally be the same color as said device or a different color from said device;

at least one needle hub adapter configured to receive a syringe or trocar, each needle hub adapter having an opening extending to said bottom of the body, wherein said opening has a specific angle and depth that can be fixed or changeable; and
a set of repeated projections extending from the bottom of said body configured to facilitate gripping the outer eye surface and facilitate distribution of said medicine, antibiotic, anesthetic or any other fluid or gel that was retained in said reservoir.

* * * * *